United States Patent [19]

Hanson

[11] Patent Number: 5,578,643
[45] Date of Patent: Nov. 26, 1996

[54] PROTECTIVE PROSTAGLANDINS FOR USE IN CONJUNCTION WITH CHEMOTHERAPEUTIC AGENTS

[75] Inventor: Wayne R. Hanson, Oak Park, Ill.

[73] Assignee: Loyola University of Chicago, Chicago, Ill.

[21] Appl. No.: 286,074

[22] Filed: Aug. 4, 1994

Related U.S. Application Data

[63] Continuation-in-part of Ser. No. 886,270, May 20, 1992, abandoned.

[51] Int. Cl.$^6$ .................... A61K 31/215; A61K 31/19; A61K 31/557
[52] U.S. Cl. .................................... 514/573; 514/530
[58] Field of Search .................... 514/530, 573

[56] References Cited

U.S. PATENT DOCUMENTS

| | | | |
|---|---|---|---|
| 4,097,603 | 6/1978 | Robert | 514/530 |
| 5,324,746 | 6/1994 | McKee et al. | 514/530 |

FOREIGN PATENT DOCUMENTS

| | | | |
|---|---|---|---|
| 3705092 | 9/1988 | Germany | A61K 37/02 |
| WO94/12186 | 6/1994 | WIPO | A61K 31/557 |

OTHER PUBLICATIONS

Potten, et al. "Hair Medullary Cell Counts–a simple and sensitive indicator of radiation exposure." *Int. J. Radiat. Biol.*, 57, No. 1:13–21 (1990).

Jimenez, et al. "Biomedicine–Hair-Raising Adjunct for Chemotherapy." *Science News*, vol. 141:60 (1992).

Hussein, et al. "Protection from Chemotherapy–Induced Alopecia in a Rat Model." *Science*, vol. 249:1564–1566 (1990).

Jimenez, et al. "Protection from 1–B–D–Arabinofuranosyl-cytosine–Induced Alopecia by Epidermal Growth Factor." *Cancer Research*, vol. 52:413–415 (1992).

Torsher, et al. "Misoprostal Therapy Following Trinitrobenzene Sulfonic Acid–Induced Colitis–Accelerates Healing." *CA*, 116(23):228896W (1992).

Glover, et al. "Clinical Trials of WR–2721 Prior to Alkylating Agent Chemotherapy and Radiotherapy." *Pharmac. Ther.*, vol. 39:3–7 (1988).

W. R. Hanson, et al. *The Prostaglandin E, Analog, Misoprostol, a Normal Tissue Protector, Does Not Protect Four Murine Tumors in Vivo from Radiation Injury*, vol. 142, No. 3,. Jun. 30, 1995, pp. 281–287.

*Primary Examiner*—Kimberly Jordan
*Attorney, Agent, or Firm*—Cynthia S. Kovacevic; Roger A. Williams

[57] ABSTRACT

Prostaglandins of the PGE type can be administered in a therapeutically effective amount to protect tissue from injury resulting from chemotherapeutic agents by administering the PGE-type prostaglandin prior to administration of the chemotherapeutic agent.

20 Claims, 13 Drawing Sheets

PROTECTIVE PROSTAGLANDINS FOR USE IN CONJUNCTION WITH CHEMOTHERAPEUTIC AGENTS

This application is a continuation-in-part of U.S. application Ser. No. 07/886,270, filed May 20, 1992, now abandoned.

BACKGROUND OF THE INVENTION

The present invention provides a method for protecting a variety of normal cells and tissues from injury produced by cytotoxic agents administered for the purpose of cancer therapy (chemotherapeutic agents). Specifically, it has been found that prostaglandins can protect normal tissues, such as hair and hair follicles and the hematopoietic system including protection of white blood cell (WBC) precursors in the bone marrow, from injury resulting from the administration of chemotherapeutic agents. Other tissues which can be protected include but are not limited to the following: skin; the gastrointestinal tract including stomach (gastric tissue), small intestine, colon and colo-rectal tissue; the esophagus, the mouth, including the oral mucosa; kidney, vagina, bladder, nasal passages, and eye. Prevention of tissue injury may be beneficial in reducing the morbidity of cancer chemotherapy and/or allowing for a higher and more curative dose regimen of chemotherapy to be delivered to cancer patients without damage or with minimized damage to the normal cells of such tissues.

The present invention relates to a method for protecting a variety of types of normal cells and tissues in the body from injury produced by chemical agents commonly used in the chemotherapy of human cancer. It has been found that the systemic administration or the topical application of misoprostol, [also known as, ($\pm$)(16RS)-15-deoxy-16-hydroxy-16-methyl prostaglandin $E_1$, methyl ester and commercially available as Cytotec® from G. D. Searle & Co.] or the systemic administration of ($\pm$)methyl 7-[3$\alpha$-hydroxy-2$\beta$(4R-hydroxy-4-methyl-1E,5E,7E-nonatrienyl) 5-oxo-1$\alpha$-cyclopentyl]-4Z-heptenoate, or 16,16-dimethyl prostaglandin $E_2$ or $PGE_1$ prior to the administration of cytotoxic chemotherapeutic agents serves to protect animals from death and/or protects different cell types in normal tissues from injury or damage caused by chemotherapeutic agents.

People diagnosed as having cancer are frequently treated with single or multiple cytotoxic chemotherapeutic agents (cytotoxic agents) to kill cancer cells at the primary tumor site or at distant sites to where cancer has metastasized. Chemotherapy treatment is given either in a single or in several large doses or, more commonly, it is given in small doses 1 to 4 times a day over variable times from weeks to months. There is a large number of cytotoxic agents used to treat cancer and the mechanisms of the cytotoxic effects of each agent is frequently not known or only partially known. Irrespective of the mechanism, useful chemotherapeutic agents are known to injure and kill cells of both tumors and normal tissues. The successful use of chemotherapeutic agents to treat cancer depends upon the differential killing effect of the agent on cancer cells compared to effects on critical normal tissues. The effects of chemotherapeutic agents on normal tissues are referred to as side-effects of cancer treatment. The immediate side effects (minutes to a few hours) of chemotherapy may include dizziness, nausea, vomiting, and diarrhea. These side effects are uncomfortable but, in themselves, are not life-threatening. Cell killing or damage within normal tissues that occurs from days to weeks during a course of chemotherapy may result in uncomfortable and/or life threatening side effects. Among these effects are hair loss, hearing loss, sterility, damage to the mucosal epithelium of the gastrointestinal tract, damage to the oral mucosa, esophagus, small and large intestines, kidney damage, skin damage, cardiac damage, killing and suppression of the white blood cells which can lead to infection, and killing of hematopoietic blood forming cells. Many of these side effects are related to tissues and organ systems that have a high number of dividing cells (proliferative cells). Some of these side effects are non-life threatening; however, a reduction or prevention of these effects could have a beneficial effect on cancer patients or make it possible to administer a higher dose of the chemotherapeutic agent while minimizing damage or death of cells in normal tissue.

Hair loss (alopecia) caused by chemotherapeutic agents is an example of a non-life-threatening side effect which can be prevented or minimized. Alopecia is typically viewed by both male and female patients as a sign of rapid progress of their disease and not as a side effect of the chemotherapy treatment. Alopecia frequently produces anxiety and a loss of self esteem in cancer patients. A reduction or prevention of non-life threatening side effects of chemotherapy such as alopecia could increase a cancer patient's quality of life and outlook during treatment.

Other side effects of chemotherapy treatment are life threatening and thus limit the doses of chemotherapeutic agents that can safely be delivered to a cancer patient undergoing treatment. A reduction or prevention of dose-limiting, life-threatening side effects of chemotherapy could reduce the risk of injury or death of normal cells in the patient and possibly allow the administration of a larger dose of chemotherapeutic agents, thereby increasing the longevity and the number of survivors following chemotherapy.

Prevention or protection from the side effects of chemotherapy would be a great benefit to cancer patients. Previous efforts to reduce these side effects have been many, varied and largely unsuccessful. For non-life-threatening side effects, little effort has been expended. Attempts to prevent hair loss, for example, have included use of a cold cap or tourniquets to reduce drug concentrations in the scalp. Patient compliance is poor and these methods are infrequently used. More recently, a compound called ImuVert (made by Cell Technology, Inc.) has been reported to reduce hair loss in rats given anti-cancer agents, but the flu-like side effects make it impractical (See Hussein, A. M.; Jimenez, J. J.; McCall, C. A.; Yunis, A. A., Protection from Chemotherapy Induced Alopecia in a Rat Model. Science 249:1564–1566; 1990).

For life-threatening side effects, efforts have concentrated on altering the dose and schedules of the chemotherapeutic agent to reduce the side effects. Other options are becoming available, such as the use of colony stimulating factor (CSF), granulocyte-macrophage-CSF (GM-CSF) or epidermal growth factor (EGF) to increase the number of normal cells in various tissues before the start of chemotherapy (See Jimenez, J. J.; Yunis, A. A. Protection from 1-$\delta$-D-Arabinofuranosylctosine-Induced Alopecia by Epidermal Growth Factor and Fibroblast Growth Factor in the Rat Model. Cancer Research 52:413–415; 1992). The mechanisms of protection by these factors, while not fully understood, are most likely associated with an increase in the number of normal critical target cells before treatment with cytotoxic agents.

There are few compounds which provide direct protection from injury caused by chemotherapy. One agent that has been reported to protect the kidney from injury caused by bolus infusions of cisplatin is S-2-(3-aminopropylamino) ethylphosphorothioxic acid (WR2721). (See Glover, D.; Fox, K. R.; Weiler, C.; Kligerman, M. M.; Turrisi, A.; Glick, J. H. Clinical Trials of WR-2721 Prior to Alkylating Agent Chemotherapy and Radiotherapy. Pharmacology and Therapeutics 39:3; 1988). This compound appears to have limited usefulness and is effective only for large single doses of the chemotherapy agent, since WR-2721 itself given in large protective doses causes hypotension, nausea, and vomiting in humans. These toxicities increase with daily use and, as a result, have been found ineffective given over the days to weeks of typical chemotherapy regimens.

It would be desirable to provide effective protection from chemotherapy side effects. It would be desirable to provide such protection by a simple procedure which would assure compliance and not interfere with the beneficial therapeutic properties of the chemotherapy agents.

Prostaglandins are known for their protective properties associated with the gastric and intestinal mucosa. They are recognized for their protective properties with respect to ethanol-induced injury to the G.I. tract, NSAID induced injury to the G.I. tract and to radiation-induced injury. The mechanism associated with ethanol injury appears to be related to mucous secretion and/or bicarbonate secretion. There is no apparent causal link between prostaglandins and WR-2721 which compound has been shown to protect from cisplatin injury.

U.S. Pat. No. 4,081,553 (to Robert), provides a method for the treatment of intestinal inflammatory disease caused by radiation exposure, as well as a method of treatment for Crohn's disease, inflammatory bowel disease, infectious enteritis, sprue and intestinally manifested allergic responses to foodstuffs by administering a cytoprotective prostaglandin to a patient suffering from one of these diseases. Such cytoprotective prostaglandins modify inflammatory infiltration into gastric or intestinal tissue and are administered after injury to the tissue.

U.S. Pat. No. 4,097,603 (to Robert) discloses a method of protecting gastric tissue from gastric inflammatory disease and ulcerative (erosive) diseases by administration of prostaglandins, including prophylactic administration 30 minutes prior to administration of an inflammation causing agent. The type of injuries to gastric tissue discussed by Robert are injuries resulting from inflammation of such tissue. Robert mentions that suitable subjects for treatment by the disclosed methodology include patients exposed to noxious agents such as household cleaners and chemotherapeutic agents.

The mechanisms of protection by prostaglandins of gastric and intestinal tissue are associated with increased mucous secretion or increased bicarbonate secretion. (See T. A. Miller, Am. J. Physiol., 245:G601–G623, 1983). Such increased secretions are unique to the physiology of gastric and intestinal tissue and such mechanisms would not be possible in non-mucous and/or non-bicarbonate secreting tissue.

The present invention provides cell protection for several non-mucous producing and non-bicarbonate producing tissues, such as hair follicles, bone marrow and skin, from cell injury caused by chemotherapeutic agents. Additionally, the present invention provides for protection of normal tissue from actual cell death which is distinct from the protection of stomach and intestinal tissue from inflammatory diseases. Thus, it is postulated that the mechanism of action of the E-type prostaglandins of the present invention is unique and distinct from the proposed mechanism of action of PG induced protection of stomach tissue or intestinal tissue from inflammation.

SUMMARY OF THE INVENTION

The present invention provides a method for protecting non-stomach tissue in a mammal from injury resulting from chemotherapeutic agents comprising, administering, prior to the administration of such chemotherapeutic agent, a therapeutically effective amount of an E-type prostaglandin. More preferably the E-type prostaglandin administered is selected from the group consisting of:

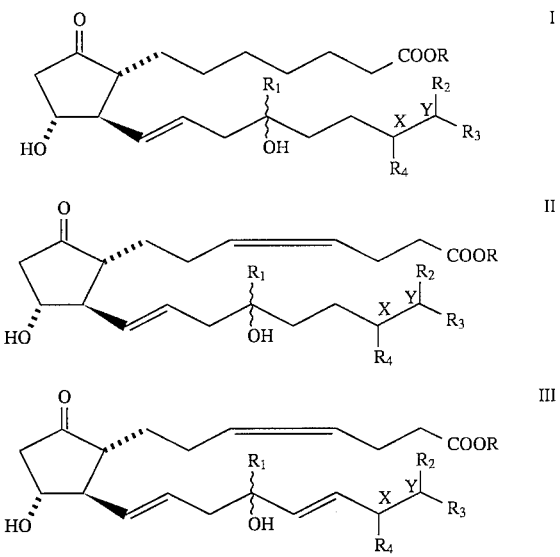

16,16-dimethyl $PGE_2$; and $PGE_1$.

wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X–Y bond can be saturated or unsaturated. Most preferably the E-type prostaglandin administered is misoprostol.

DETAILED DESCRIPTION

Figure 1:
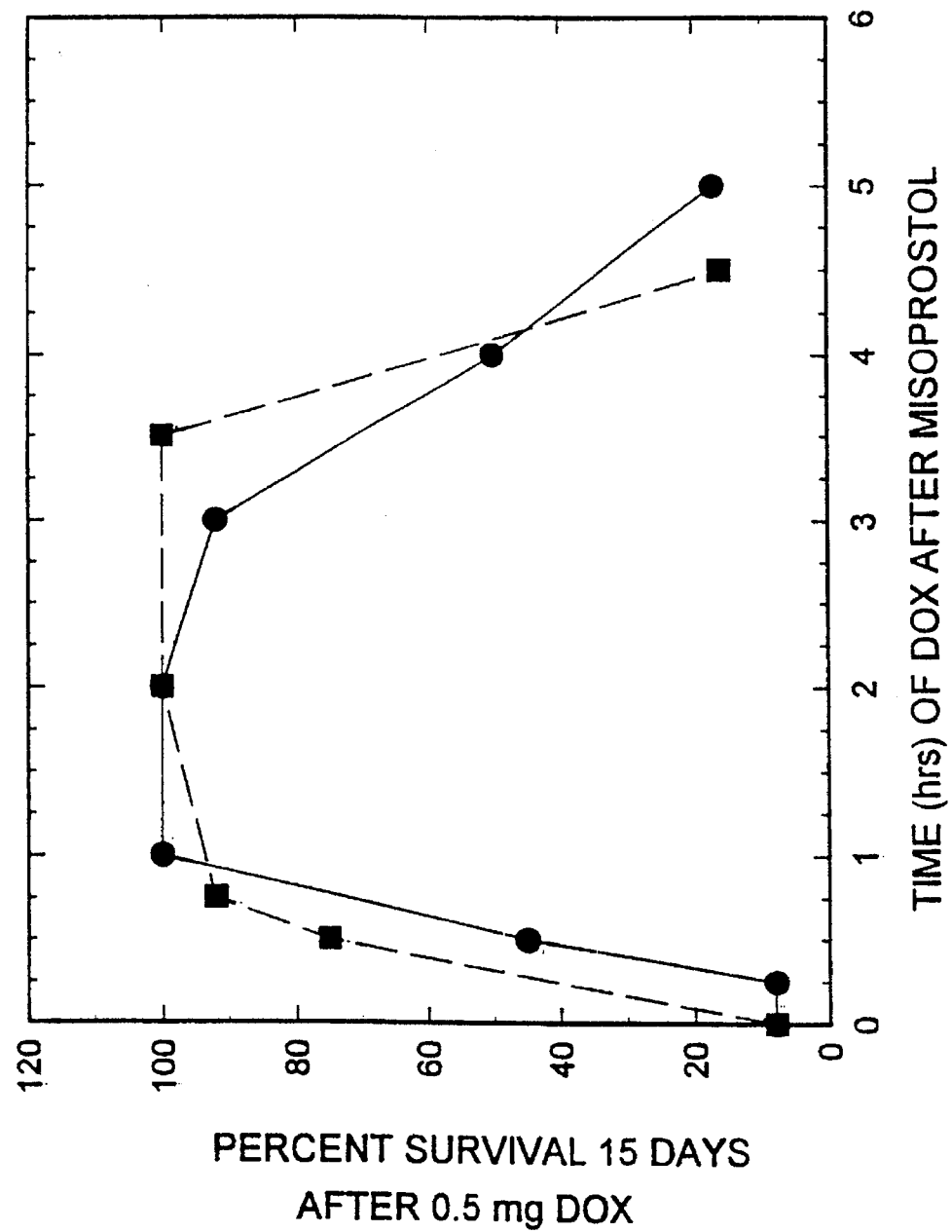
FIG. 1 is a graph illustrating percent survival of mice over 15 days as a function of the time interval (in hours) between the administration of misoprostol and the subsequent administration of doxorubicin. (The two curves represent duplicate experiments; 12 animals per experiment.)

The present invention provides a method for protecting non-stomach tissue in a mammal from injury resulting from chemotherapeutic agents comprising, administering, prior to the administration of such chemotherapeutic agent, a therapeutically effective amount of an E-type prostaglandin. More preferably the E-type prostaglandin administered is selected from the group consisting of:

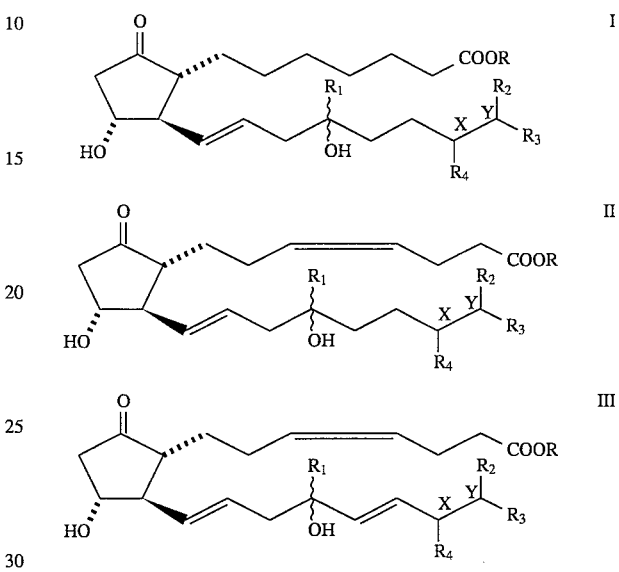

16,16-dimethyl $PGE_2$; and $PGE_1$, wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X–Y bond can be saturated or unsaturated. Most preferably the E-type prostaglandin administered is misoprostol.

The invention further provides for the systemic or topical administration of such E-type prostaglandins, and more specifically provides for administration of the prostaglandins ½ hour to 3 hours prior to administration of the chemotherapeutic agent. The invention further provides for a method for inhibiting the reduction of lymphocytes in a mammal being treated with a lymphocyte-reducing chemotherapeutic agent, by administration of a therapeutically effective amount of the E-type prostaglandins described above. The invention provides protection for the cells of normal tissue from injury or cell death resulting from administration of chemotherapeutic agents.

As used herein the term "cell death" refers to the loss of reproductive integrity or clonogenic capacity resulting from the activity of the chemotherapeutic agent.

Protection of normal tissue of cancer patients from injury or cell death caused by systemic administration of chemotherapeutic agents may be accomplished by administering the prostaglandins herein, topically in an appropriate vehicle, to surface structures such as hair follicles, skin, oral and pharyngeal mucosa, esophagus, colon, rectum, bladder, vagina, or any organ on the outside of the body or internally where there is a luminal surface which can be reached non-invasively. Topical administration is especially suitable for protection of hair follicles and the oral mucosa. The protection of internal organs such as bone marrow, kidney, small intestine, liver, brain, gonads or any other normal internal organ suspectable to chemotherapy injury may be achieved by administration of a prostaglandin herein by any technique capable of introducing the compound into the blood stream of a patient, including oral administration and by intravenous, intramuscular and subcutaneous injections.

Prostaglandin compounds indicated for protection of normal tissue from injury or cell death by chemotherapeutic agents can be administered from about 30 minutes to about 3 hours before administration of a chemotherapeutic agent and more preferably the prostaglandins are administered about 1 hour to about 3 hours prior to administration of a chemotherapeutic agent. Most preferably the prostaglandin is administered from about 1.5 hours to about 2.5 hours before administration of a chemotherapeutic agent. While some protection may be provided by administering the prostaglandins outside of these ranges, greater protection is provided within this range.

The dosage of protective prostaglandins administered will depend upon patient condition and symptomology. The therapeutically effective amount of prostaglandin administered will be in an amount of about 0.010 μg up to about 50 μg per kilogram of body weight per day. A more preferred dosage range is from about 0.1 μg to about 20 μg per kilogram of body weight. The most preferred dose is in an amount from about 0.2 μg to about 10.0 μg per kilogram of body weight per day. A suitable dose can be administered in multiple sub-doses per day. These sub-doses can be administered in unit dosage forms. Typically, a dose or sub-dose may contain from about 5.0 μg to about 800 μg of active compound per unit dosage form. A more preferred dosage can contain from about 10 μg to about 400 μg of active compound per unit dosage form. The most preferred dosage form containing from about 10 μg to about 200 μg of active compound per unit dose.

The active compound can be administered in a pharmaceutically-acceptable formulation. Such formulations may comprise the active E-type prostaglandin together with one or more pharmaceutically-acceptable carriers or diluents. Such formulations may comprise more than one of the active E-type prostaglandins. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules or tablets containing the active compound dispersed in a binder such as gelatin or hydroxypropylmethyl cellulose, together with one or more of a lubricant, preservative, surface-active agent or dispersing agent. Such capsules or tablets may contain a controlled-release formulation as may be provided by a dispersion of active compound in hydroxypropylmethyl cellulose.

Formulations for parenteral administration may be in the form of aqueous or nonaqueous isotonic sterile injection solutions or suspensions. These solutions and suspensions may be prepared from sterile powders or granules having one or more of the carriers or diluents mentioned for use in the formulations for oral administration.

The following examples describe and illustrate embodiments of the present invention. These examples are meant to be illustrative of the present invention and not limiting thereof in either scope or spirit.

BIOLOGICAL EVALUATION

The utility of the prostaglandins herein as protectors from damage to normal tissue caused by chemotherapeutic agents used to treat human cancer, is demonstrated by the following assays and results.

EXAMPLE 1

Mortality of mice is a measure of PG-induced protection from death due to severe normal tissue injury inflicted by chemotherapy agents.

This assay was accomplished by injecting intraperitoneally (IP) separate groups of mice with a range of doses of chemotherapeutic agents. The dose range of each chemotherapeutic agent varied between low doses which caused no death to high doses that caused 100 percent death within a specified time. In some groups of mice, longevity was recorded by plotting the number of animals remaining alive (percent survival) versus time following the administration of the chemotherapeutic agent.

PG-induced protection from the toxic chemotherapeutic agents was measured by subcutaneous (SC) injection of the PG at various times prior to or after the IP administration of the chemotherapeutic agent. FIG. 1 shows the percent of mice that survived for 15 days as a function of the time interval (in hours) between administration of misoprostol and the chemotherapeutic agent, doxorubicin (DOX). The time interval was varied from 15 minutes to 5 hours. The two curves represent two separate experiments with 20 mice in each experiment. The "0" time point is the percentage of mice that survived 15 days after administration of doxorubicin alone. The results show that the optimum time interval to achieve near maximum misoprostol-induced protection when given prior to administration of doxorubicin is from about 1 to about 3 hours.

Figure 2:
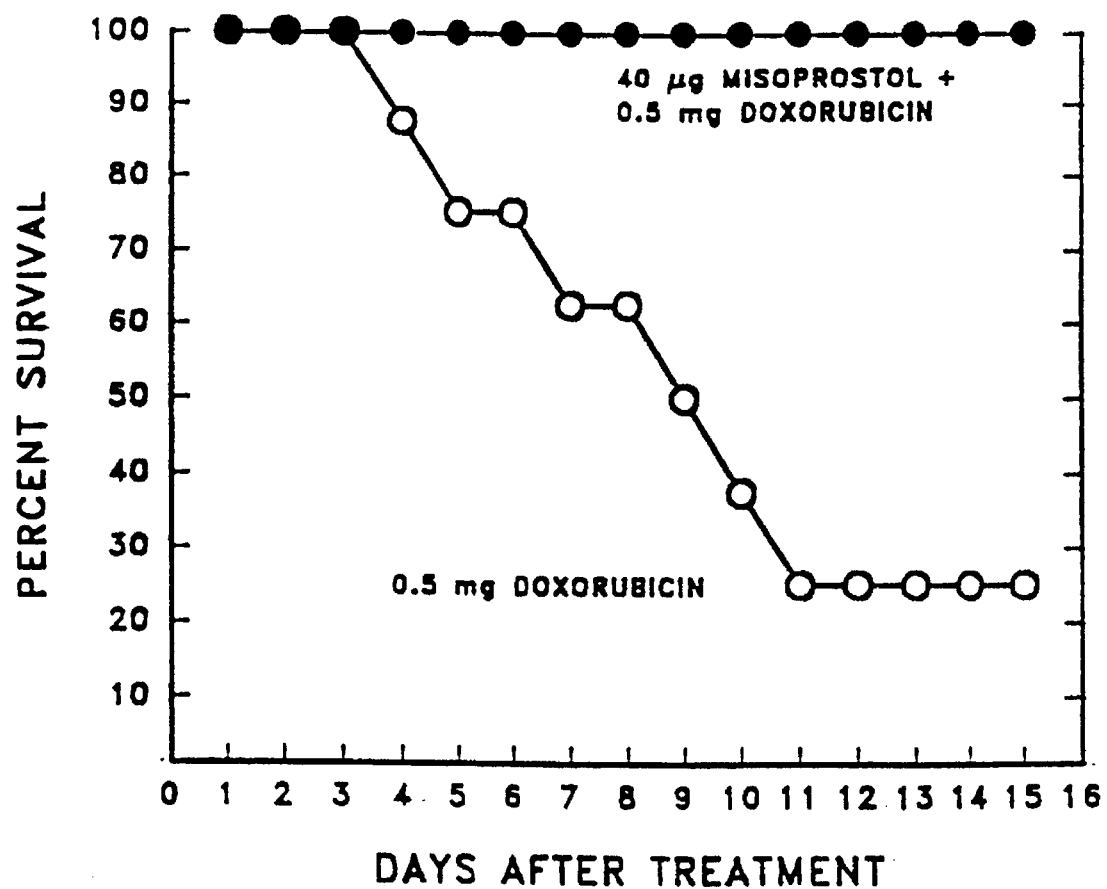
FIG. 2 is a graph illustrating the percent survival of mice over 15 days following the administration of 0.5 mg of doxorubicin (open circles) and mice given 40 µg of misoprostol 2 hours before administration of 0.5 mg of doxorubicin (filled circles). (N=16 for each group).

FIG. 2 shows percent survival of mice (n=16) given 0.5 mg of doxorubicin (DOX) and a separate group of mice (n=16) given 40 μg of misoprostol 2 hours before administration of 0.5 mg of doxorubicin. By 15 days after administration of DOX alone, about 25% of the mice still survived. Of the group of mice that received the misoprostol before DOX, 100% of the mice were still alive after 15 days. Statistical analysis using the Life Table algorithm in the 4.01 version of SPSS/PC+software (SPSS Inc., Chicago, Ill.) showed a p value of ≤0.001.

Figure 3:
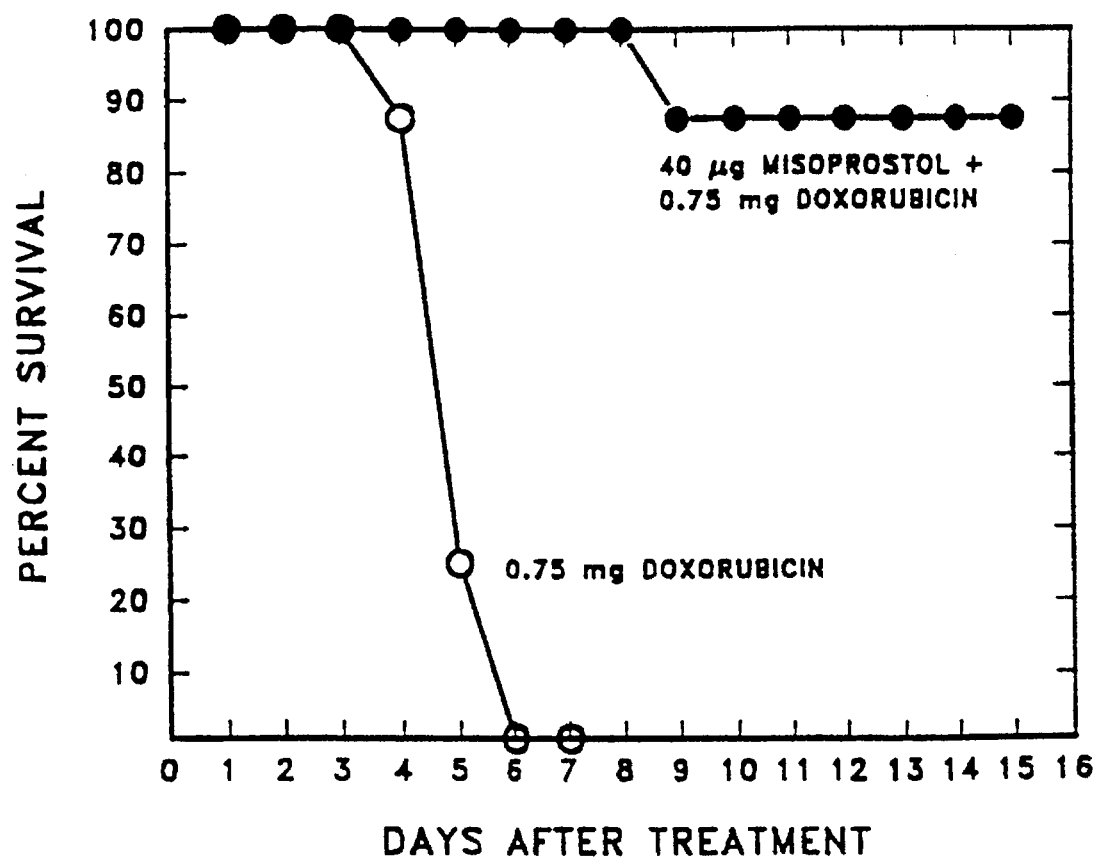
FIG. 3 is a graph illustrating the percent survival of mice over 15 days following the administration of 0.75 mg of doxorubicin (open circles) and mice given 40 µg of misoprostol 2 hours before administration of 0.75 mg of doxorubicin (filled circles). (N=16 for each group).

FIG. 3 shows data similar to that in FIG. 2; however, one group of mice (n=16) was given 0.75 mg of DOX/mouse and the other group of mice (n=16) was given 40 μg misoprostol 2 hours before administration of 0.75 mg of DOX. All of the mice were dead by six days following the I.P. administration of 0.75 mg of DOX alone. Of the group of mice given 40 μg misoprostol 2 hours before 0.75 mg of DOX, about 85% were still alive by day 15. There was a statistically significant difference at the p≤0.001 value for these data.

Figure 4:
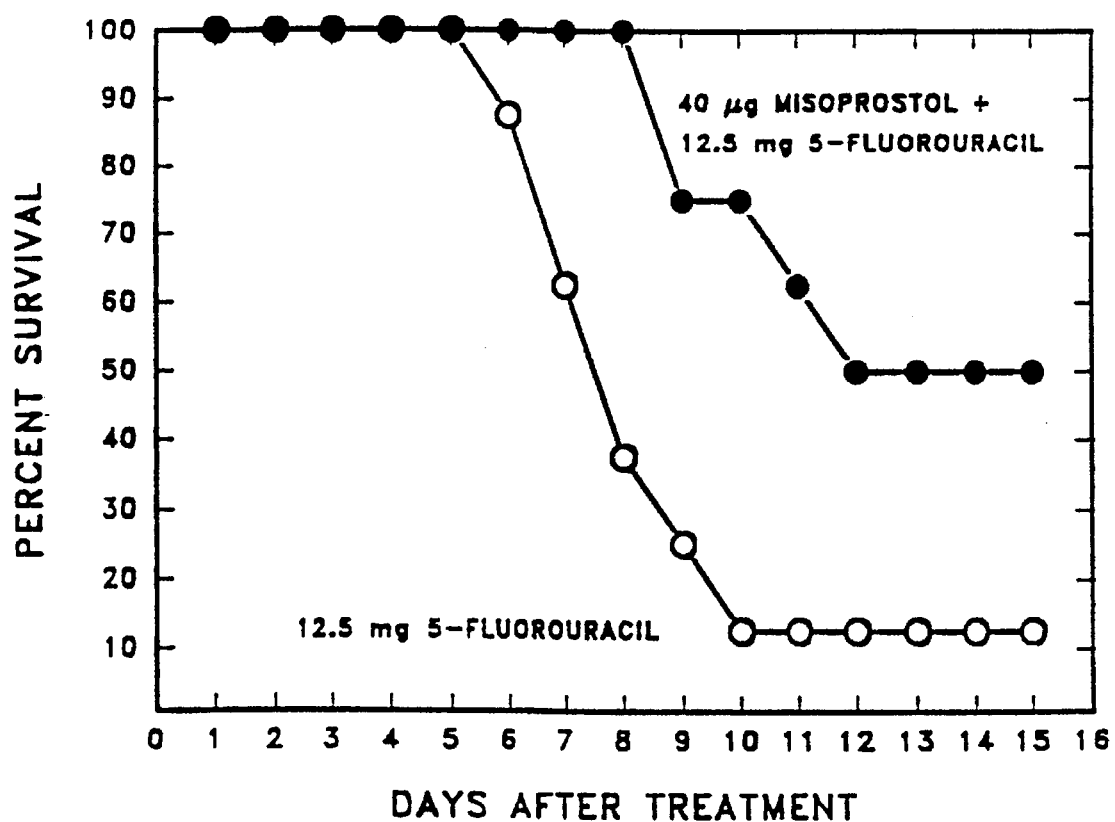
FIG. 4 is a graph illustrating the percent survival of mice over 15 days following the administration of 12.5 mg of 5-fluorouracil (open circles) and mice given 40 µg of misoprostol 2 hours before administration of 12.5 mg of 5-fluorouracil (filled circles). (N=8 for each group).

The toxicity of 12.5 mg of 5-fluorouracil alone to mice and the effectiveness of 40 μg of misoprostol given 2 hours prior to administration of 5-fluorouracil to protect from death due to 5-fluorouracil is shown in FIG. 4. The data indicates that misoprostol was effective in protecting mice from damaging effects of 5-fluorouracil. The life table analysis showed that with an n of 8, the p value was ≤0.05.

Figure 5:
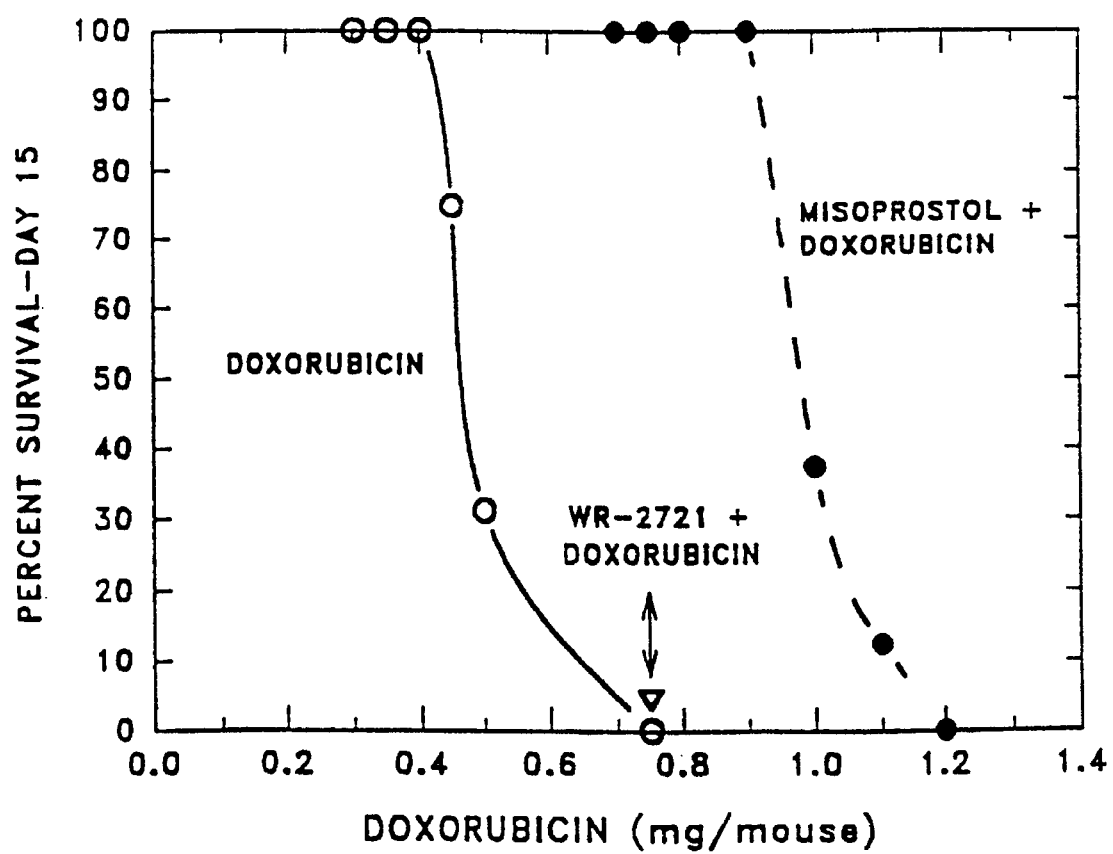
FIG. 5 is a graph illustrating the percent survival of mice 15 days following administration of graded doses of doxorubicin (open circles) and mice given 40 μg of misoprostol 2 hours before administration of graded doses of doxorubicin (filled circles). The open triangle is data of a group of 10 mice given WR-2721, 30 minutes before administration of 0.75 mg of doxorubicin. (The lines are computer fit spline curves through the data; n=24 per data point on each curve).

It was observed that all acute deaths due to DOX treatment alone occurred before day 15 following DOX administration. Subsequently, the parameter of death within 15 days was used to investigate the DOX dose response administered IP alone or 2 hours after 40 µg of misoprostol was given subcutaneously (sc). In this study, a dose of about 0.5 mg of DOX/average 30 gram mouse, killed 50% of the DOX treated mice (see FIG. 5). In groups of mice given 40 µg of misoprostol 2 hours before administration of graded doses of DOX, the dose required to kill 50% of the population of mice, was increased to about 1.0 mg of DOX/average 30 gram mouse.

In order to provide protection, the PG had to be given before the chemotherapeutic agent. Administration of the PG 5 minutes or 1 hour after administration of DOX afforded no protection to DOX treated mice (data not shown).

Figure 6:
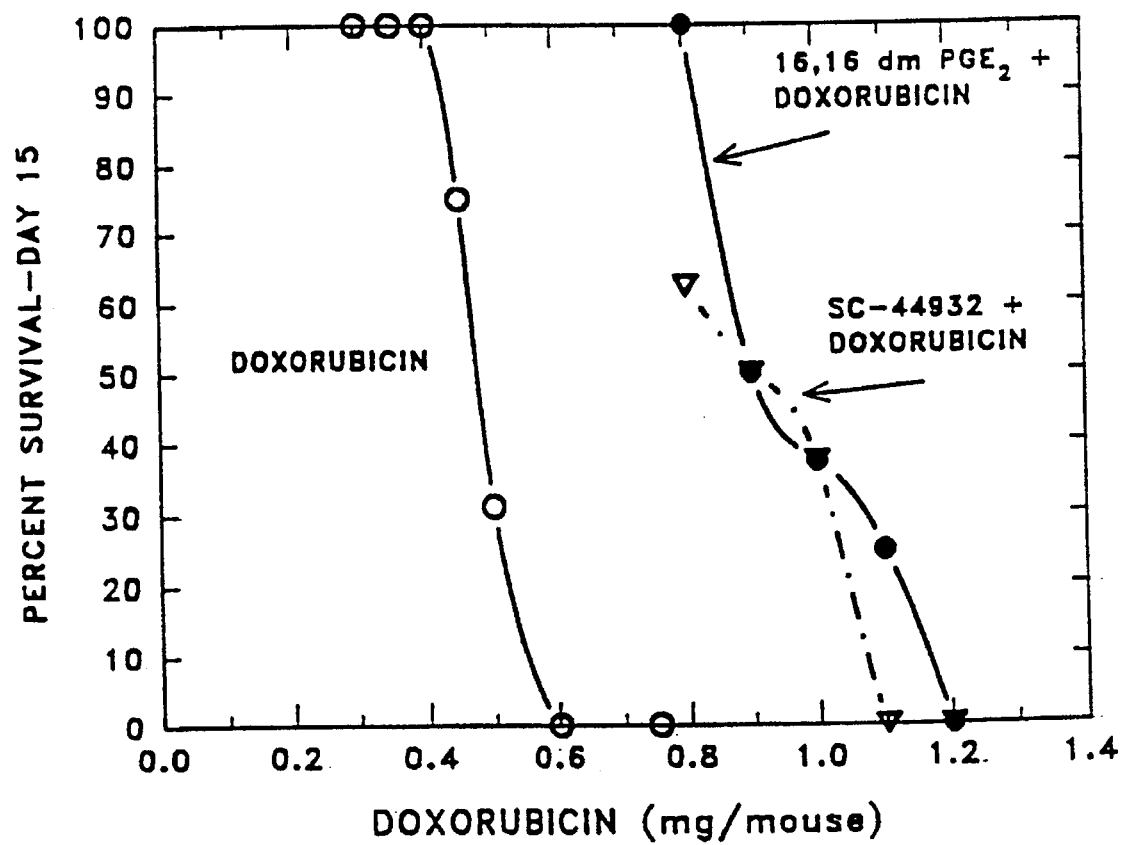
FIG. 6 is a graph illustrating the percent survival of mice over 15 days following administration of graded doses of doxorubicin (open circles) and of mice given 10 μg of 16,16-dimethyl $PGE_2$ (open circles) or 25 μg (±)methyl, 7-[3α-hydroxy-2β-(4R-hydroxy-4-methyl-1E,5E,7E-nonatrienyl)-5-oxo-1α-cyclopentyl]-4Z-heptenoate (open triangles) 2 hours before administration of graded doses of doxorubicin (filled circles). (The lines are computer fit spline curves through the data; n=8 per data point for each of the PG-treated groups and n=24 for the data points of mice treated only with doxorubicin).

A comparison of PG-induced protection was made to that of protection by WR-2721; an agent reported to protect from some chemotherapeutic agents. WR-2721 did not protect mice (n=10) from DOX treatment, (see FIG. 5). Two other PGs representing different structural prostaglandins than misoprostol were also investigated for their effectiveness in protecting mice from mortality resulting from administration of graded doses of DOX. Ten µg of 16,16-dimethyl $PGE_2$ and 25 µg of (±) methyl, 7-[3α-hydroxy-2β-(4R-hydroxy-4-methyl-1E, 5E,7E-nonatrienyl)-5-oxo-1α-cyclopentyl]-4-Z-heptenoate (also known as SC-44932) increased the DOX dose necessary to kill 50% of a population (n=8) of mice (see FIG. 6). The degree of protection by these PGs was similar to that seen for misoprostol.

Figure 7:
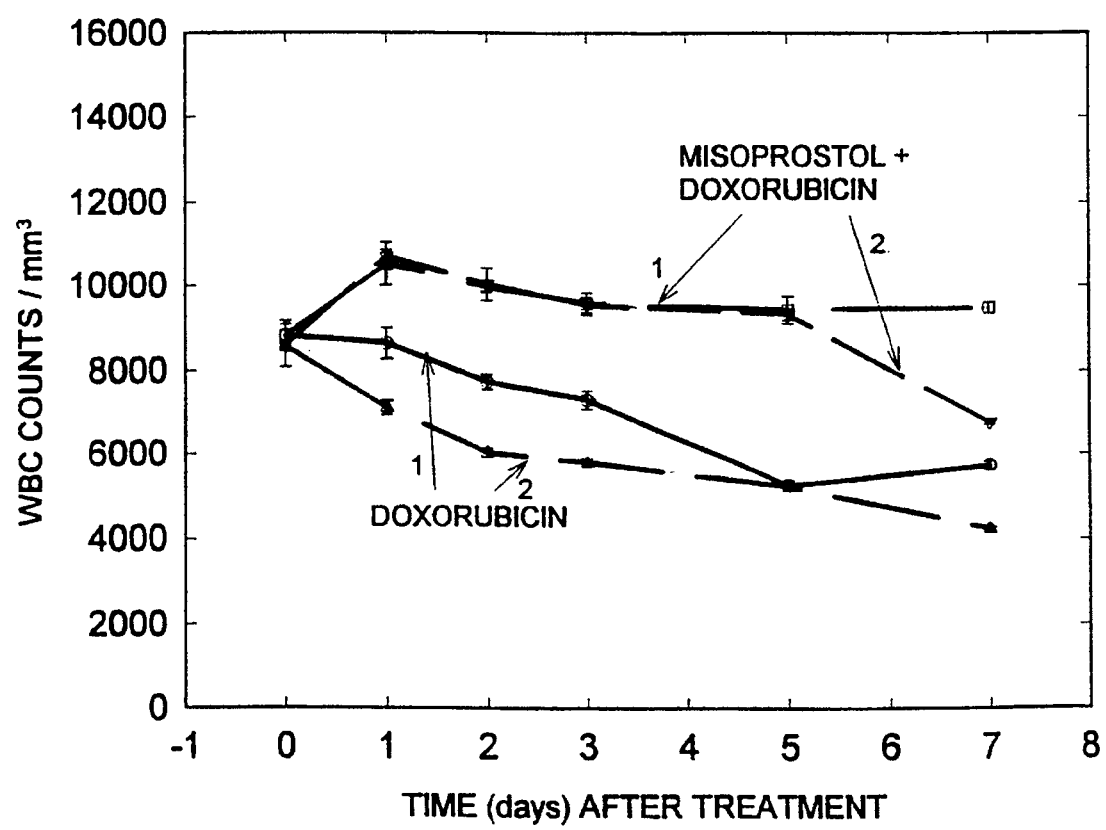
FIG. 7 is a graph illustrating the protective effect of misoprostol (given 2 hours before doxorubicin) on WBC counts compared to the effect of doxorubicin alone on WBC counts as function of time (in days). (The numbers 1 and 2 are duplicate studies.)

The mechanism by which PGs protect from chemotherapeutic agents is not known; however, evidence suggests that several tissues are protected. Death within 15 days of DOX treatment alone is most likely associated with bone marrow injury. The white blood cells (WBCs) in the peripheral circulation of DOX treated mice (0.5 mg DOX/30 gram mouse) were sharply reduced over 7 days following treatment (See FIG. 7). In mice given misoprostol (40 µg/30 gram mouse) 2 hours before DOX administration, the WBC counts remained near control levels. Since the turnover of circulating WBC is rapid (6 hours for neutrophils and within 1 to 3 days for many lymphocytes) these data suggest that misoprostol protects the WBC precursors in bone marrow from DOX injury. Differential counts showed that the percentage of lymphocytes was reduced from about 85% in control mice to less than 10% in mice given 0.5 mg of DOX. DOX, therefore, appears to not only reduce the total WBC, but has a particularly marked effect on lymphocytes. Differential counts of peripheral blood showed that the percentage of lymphocytes was increased from less than 10% in mice given 0.5 mg of DOX to greater than 30% in mice given 40 µg of misoprostol 2 hours before administration of 0.5 mg of DOX.

Another example showing that PGs protect a variety of tissues from injury from chemotherapeutic agents is shown in the next example.

EXAMPLE 2

Amount of Hair Loss as a Measure of PG-induced Protection from Alopecia caused by Chemotherapeutic Agents.

One of the side effects of chemotherapy in cancer patients is hair loss or alopecia. Studies were conducted to measure a possible protective effect of PGs from alopecia caused by chemotherapeutic agents. The chemotherapeutic agents used for these studies were DOX and cytoxan (CTX). The hairs on the rumps of mice (n=4/group) were plucked to induce a growth or anagen cycle within hair follicles which continues for about 18 days. Ten days after plucking, 5 daily treatments of DOX (0.1 mg/average 30 g mouse/day) or CTX (1.0 mg/average 30 g mouse/day) were administered I.P. In separate groups of plucked mice, misoprostol was given S.C. 2 hours before each dose of DOX or CTX. Control groups (n=4) received no treatment or misoprostol alone.

Figures 8A, 8B, 8C:
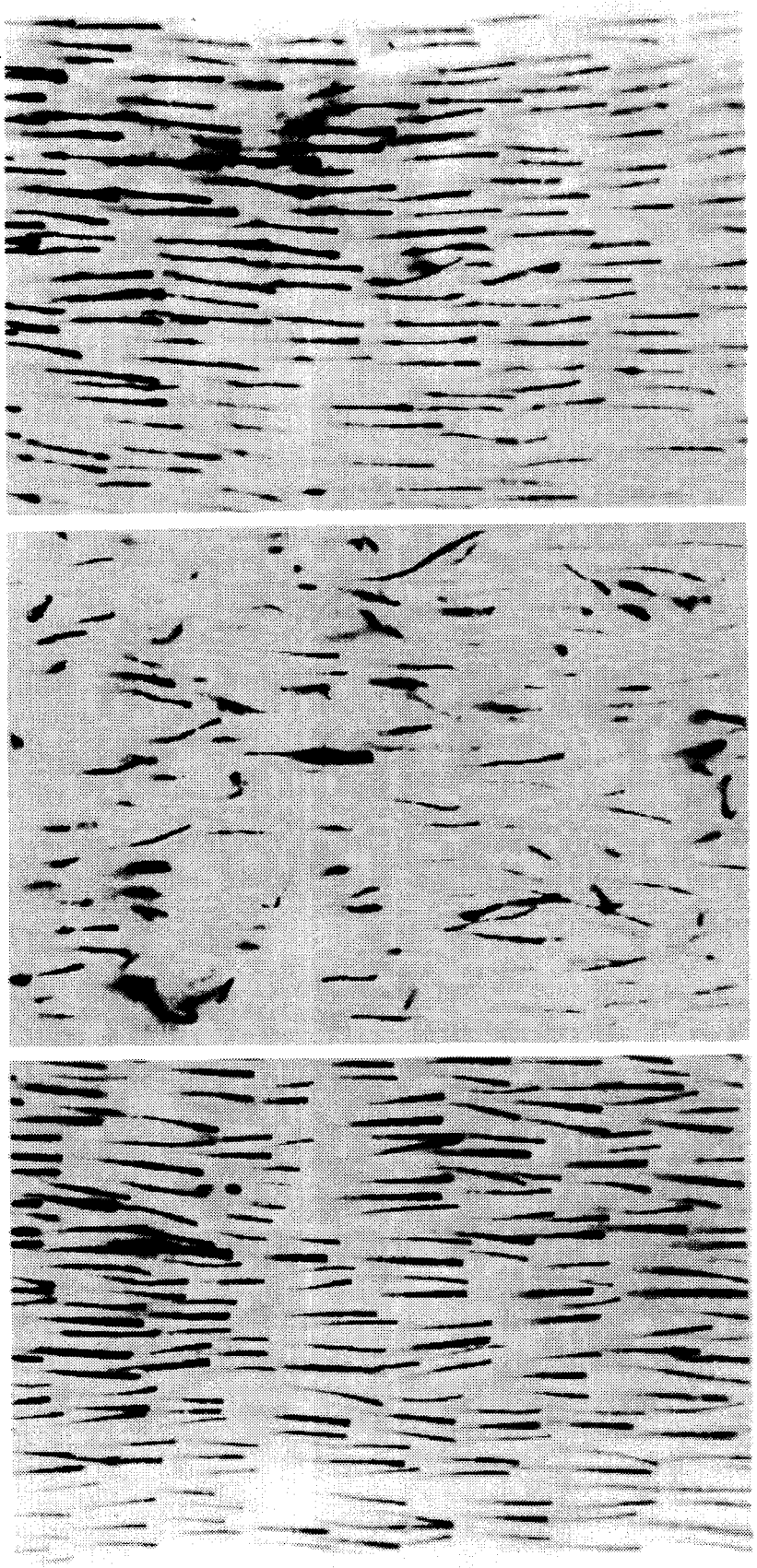
FIG. 8 is a representation of low power (30×) photomicrographs of hair from a 4.42 sq mm area of rump skin in an untreated control animal (Panel A) and from an animal treated for 5 days with a 0.1 mg daily dose of doxorubicin (Panel B). Panel C is a representation of a photomicrograph of an animal given 40 μg of misoprostol, 2 hours before the 0.1 mg daily dose of doxorubicin given each day for 5 days. Average hair counts are presented in FIG. 9.

All mice were killed 2 weeks after the initiation of the treatments and the number of hairs in 4.42 sq. mm areas were counted and averaged (2 fields per sample). Panel A of FIG. 8 shows a representative field of untreated control hair under low power light microscopy. Panel B of FIG. 8 shows a representative field of damage to hair in mice given fractions of DOX for 5 days. Panel C of FIG. 8 shows a representative field from mice given misoprostol 2 hours before each of the daily treatments of DOX. The appearance of the hair in misoprostol plus DOX treated mice (Panel C) is similar to the appearance of normal untreated hair (Panel A).

Figure 9:
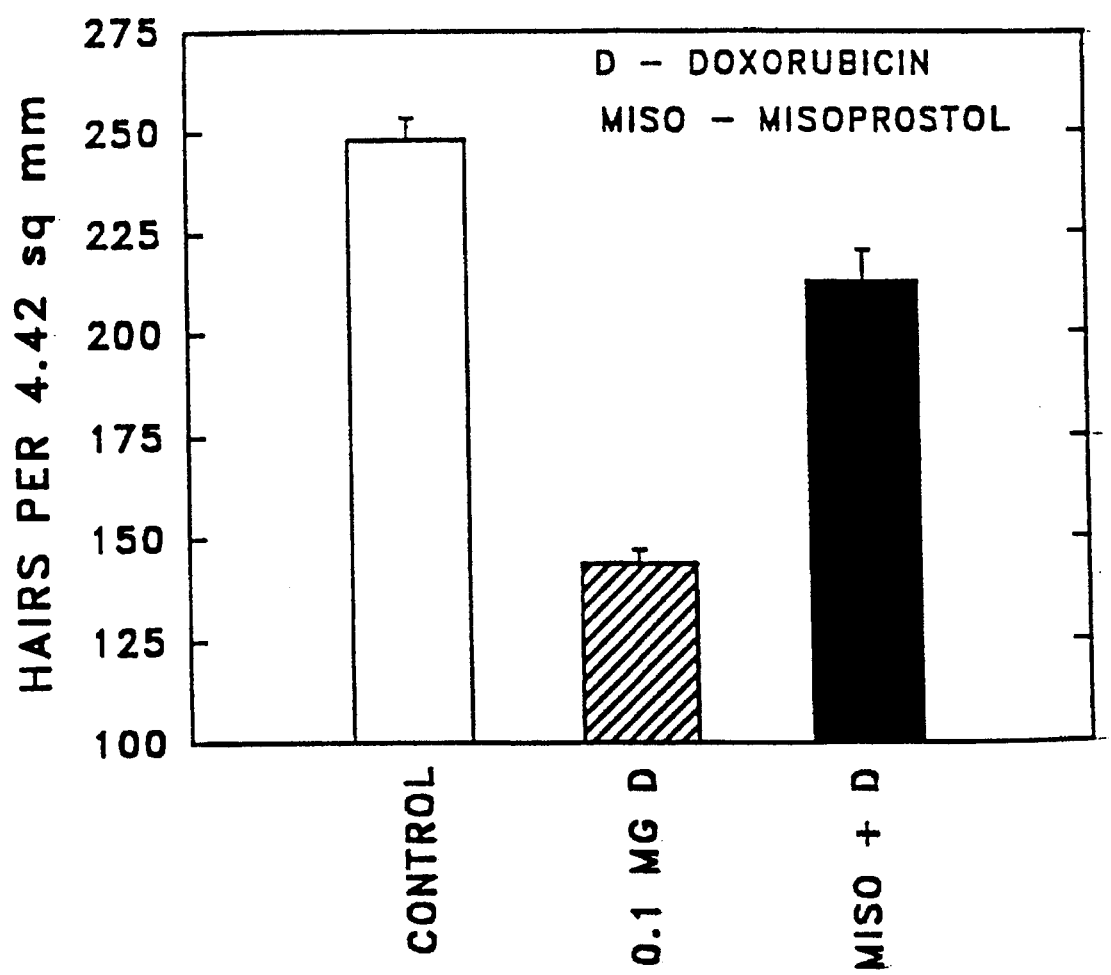
FIG. 9 is a graph illustrating the number of hairs per 4.42 sq. mm of skin area in control mice, in mice that received 0.1 mg of doxorubicin daily for 5 days or in mice that received 40 μg of misoprostol 2 hours before each of the daily doses of doxorubicin given for 5 days. (Data are the means of 6 mice (2 fields/mouse)±1 SEM.)
Figure 10:
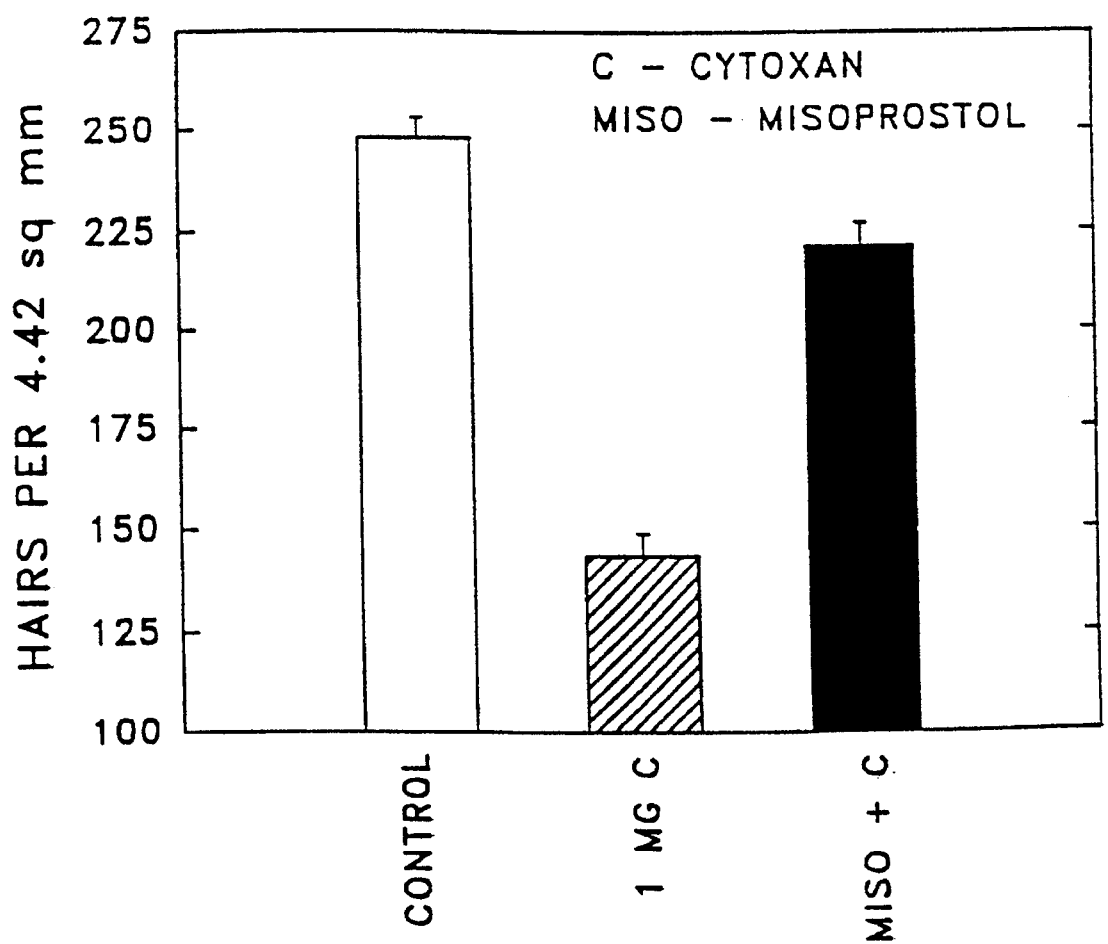
FIG. 10 is a graph illustrating the number of hairs per 4.42 sq mm of skin area in control mice, in mice that received 1.0 mg of cytoxan daily for 5 days, and in mice that received 40 μg of misoprostol 2 hours before each of the daily doses of cytoxan given for 5 days. (Data are the means of 6 mice (2 fields/mouse)±1 SEM.)
Figure 11:
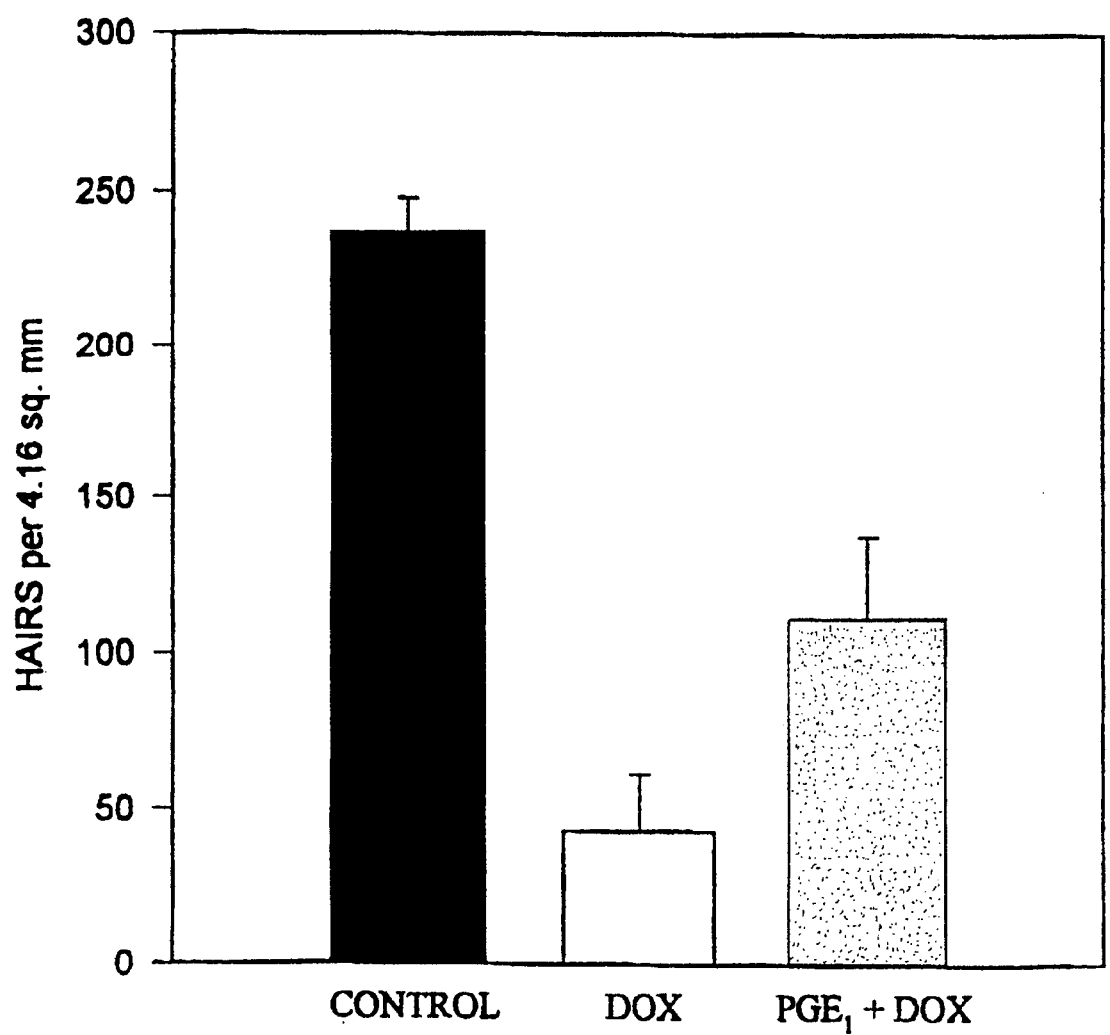
FIG. 11 is a graph illustrating the number of hairs per 4.16 sq. mm of skin area in control mice, in mice that received 0.5 mg of doxorubicin or in mice that received 10 μg of $PGE_1$ 2 hours before receiving 0.5 mg of doxorubicin. (Data are the means of 6 mice (2 field/mouse)±SEM.)
Figure 12:
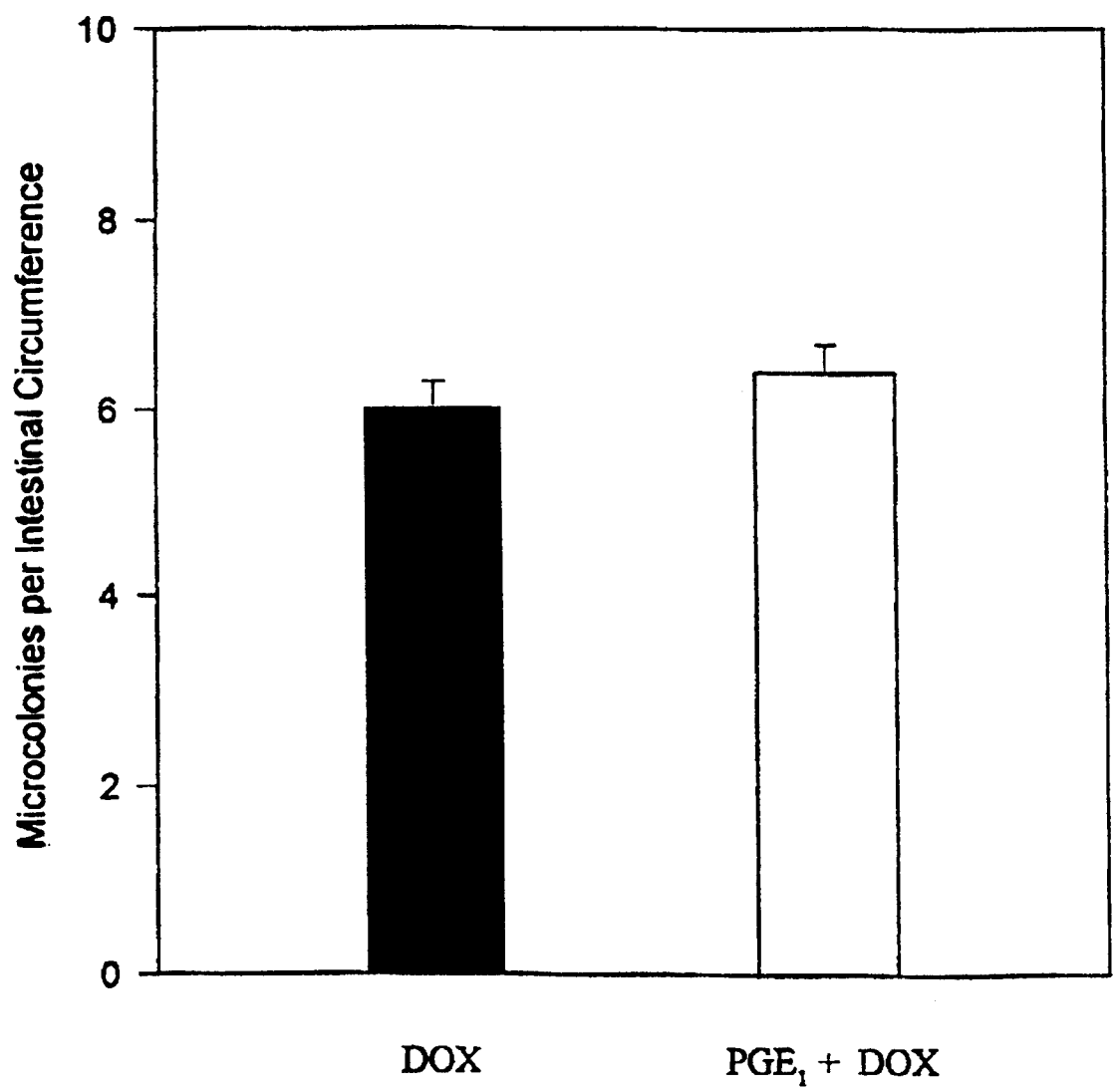
FIG. 12 is a graph illustrating the number of microcolonies per intestinal circumference in mice given 0.5 mg of doxorubicin or in mice given 10 μg of $PGE_1$ 2 hours before administration of 0.5 mg of doxorubicin. (Data are the means of 4 mice±1 SEM.)
Figure 13A:
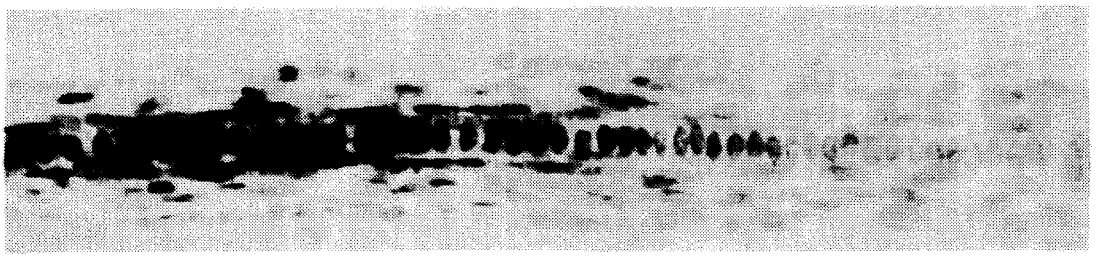
FIG. 13 is a representation of photographs of shafts of hair showing a single line of medullary cells in control mice (Panel A) and in mice 4 days after they were given a single dose of 0.3 mg of VP-16-213 (Panel B). Panel C in FIG. 13 shows a representation of a photograph of medullary cells of mice 4 days after they were given misoprostol subcutaneously 2 hours before administration of VP-16-213 and Panel D shows a representation of a photograph of medullary cells of mice 4 days after they were given misoprostol topically 2 hours before administration of VP-16-213.
Figure 13B:
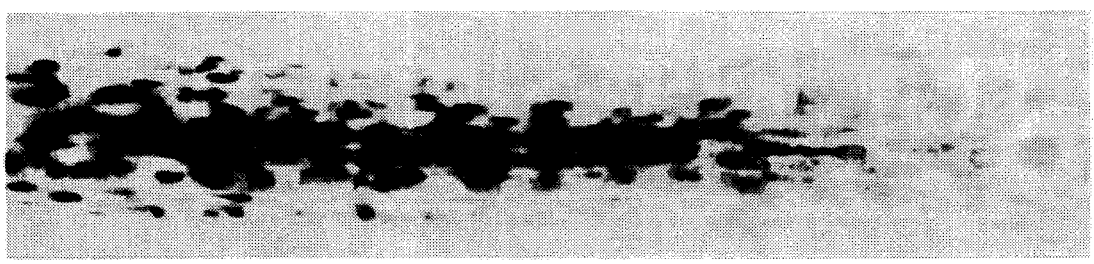
Figure 13C:
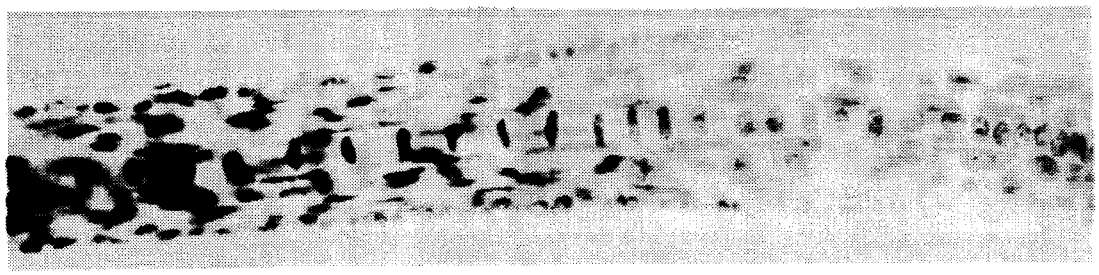
Figure 13D:
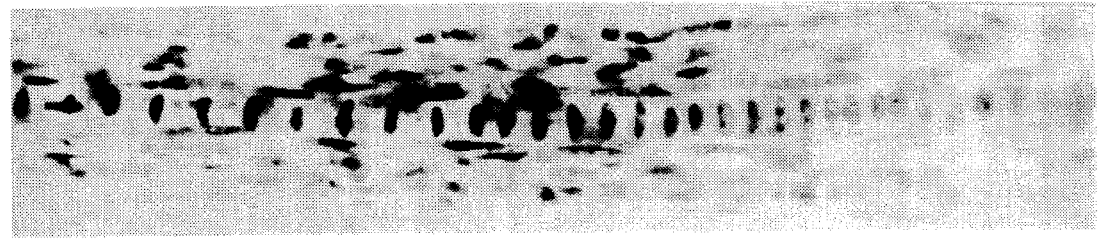

The hair counts from skin fields of control (open bar), DOX (striped bar) and misoprostol+DOX (filled bar) treated mice are shown in FIG. 9. DOX alone reduced the number of hairs from 248±5 per 4.42 sq. mm in controls to 144±3. Misoprostol given before DOX increased the hair count to 213±7.8. Similar data were found for CTX and misoprostol+CTX treated mice, see FIG. 10. The values were 248±5.5 for controls (open bar), 143±5.5 for CTX treated mice (striped bar), and 222+5.5 for misoprostol+CTX treated mice (filled bar). Evidence suggests that prostaglandin protection of tissues may be dependent upon the receptors present in the tissue. Since prostaglandin receptors are not evenly distributed, protection may not be evenly distributed. $PGE_1$ is associated with the skin (hair follicles) but not with the gut. The ability of $PGE_1$ to protect the skin (hair follicles) and the small intestine from cell injury caused by doxorubicin was tested. FIG. 11 shows the number of hairs (237±5) per 4.16 sq. mm in control mice. A single dose of 0.5 mg of doxorubicin reduced this count to 43±8. Administration of 10 µg of $PGE_1$ prior to administration of doxorubicin provided protection as indicated by the increase in the number of hairs to 111±12. In FIG. 12, the number of intestinal colonies per circumference in DOX treated mice (6±0.3) did not change when 10 pg of $PGE_1$ was given 2 hours before administration of doxorubicin. These results suggest that the E-type prostaglandin misoprostol, binds to receptors and protects a broad range of tissues whereas $PGE_1$ binds to receptors and protects a narrower range of tissues and does not protect the cells of the intestine from doxorubicin. These data provide strong evidence that misoprostol and $PGE_1$ protect hair follicles from injury resulting from the administration of chemotherapeutic agents. More evidence is presented in Example 3.

EXAMPLE 3

Number of Hair Medullary Cells as a Measure of Protection from Injury caused by Chemotherapeutic Agents.

The shafts of hair in $CF_1$ mice contain usually a single line of about 50±1 medullary cells. These cells are very sensitive to cytotoxic agents (see Potten, C. S., Geng, L., and Taylor, P., Hair Medullary Cell Counts: a Simple and Sensitive Indicator of Radiation Exposure. Int. J Radiat. Biol., 57:13–21, 1990). Single doses of cytotoxic chemotherapeutic agents greatly reduce the number of medullary cells which reach a nadir at 4 days after administration of the agent. This cell system has been used for the evaluation of misoprostol-induced protection from several chemotherapeutic agents.

CF₁ mice had hair from an area of their rump plucked to induce anagen growth as described in Example 2 above. Two weeks later, mice were divided into groups of 4 each and given the following treatments: controls (no treatment), or mice that received single doses of one of the following chemotherapeutic agents: DOX, CTX, etoposide (VP-16-213) cytosine arabinoside (ARA-C), Hydroxyurea (HU), 5-Fluorouracil (5-FU), methotrexate, bleomycin, mitomycin C, cisplatin, carboplatin or taxol. In separate groups, mice received misoprostol (40 μg/average 30 g mouse) either subcutaneously or applied topically 2 hours before each of the chemotherapeutic agents listed above. Untreated controls were used since it has been previously determined that water, or 2% EtOH in water, or phosphate buffer at pH=6.8 (the vehicles for the all agents used) had no influence on the cell counts compared to untreated controls. Twenty-five hairs from each animal of each group were dissected from Feulgen stained samples taken from the mice 4 days after treatment.

FIG. 13 shows representations of photomicrographs of the medullary cells from the hairs of control mice (Panel A), mice that received VP-16-213 (Panel B), mice that received misoprostol sc before VP-16-213 (Panel C), and mice that received misoprostol topically before VP-16-213 (Panel D). The number of medullary cells was averaged (n=4) for each treatment group and the results for all chemotherapeutic agents tested to date are presented in Table I.

TABLE I

The average number of hair medullar cells four days following treatment in mice given a single dose of several chemotherapeutic agents or in mice given misoprostol 2 hrs. before the chemotherapeutic agents

| Treatment | Number of Medullar Cells ± 1 SEM | | |
|---|---|---|---|
| | | Chemotherapeutic Agent IP | |
| | Chemotherapeutic agent IP | Misoprostol Subcutaneously | Misoprostol Topical |
| control (no treatment) | 51.4 ± 0.6 | — | — |
| DOX (0.3 mg) | 18.3 ± 1.7 | 30.0 ± 1.1 | 27.0 ± 1.3 |
| CTX (1 mg) | 22.1 ± 1.9 | 33.1 ± 1.3 | 31.5 ± 2.2 |
| VP-16-213 (0.3 mg) | 23.9 ± 2.0 | 34.4 ± 1.1 | 33.0 ± 1.6 |
| ARA-C (8 mg) | 39.0 ± 1.4 | 40.1 ± 0.7 | 43.1 ± 1.7 |
| HU (10 mg) | 34.1 ± 2.1 | 38.9 ± 0.7 | 40.7 ± 1.0 |
| 5 FU (1.0 mg) | 38.4 ± 4.1 | 37.4 ± 5.0 | — |
| Methotrexate (0.2 mg) | 38.2 ± 2.3 | 50.6 ± 0.6 | 46.7 ± 2.2 |
| Bleomycin (0.05 mg) | 30.4 ± 1.4 | 27.9 ± 1.2 | 28.1 ± 1.0 |
| Mitomycin C (0.01 mg) | 26.8 ± 4.5 | 38.2 ± 1.9 | — |
| Cisplatin (0.25 mg) | 25.9 ± 1.5 | 14.3 ± 0.4 | — |
| Carboplatin (1.0 mg) | 37.8 ± 2.4 | 31.2 ± 2.4 | — |
| Taxol (0.6 mg) | 28.0 ± 3.1 | 26.0 ± 3.5 | — |

Misoprostol afforded significant (p≤0.01) protection of medullary cells from injury caused by DOX, CTX, VP-16-213, methotrexate, mitomycin C, and for HU treated mice when the PG was administered topically. Misoprostol did not protect medullary cells in ARA-C bleomycin, HU (misoprostol given systemically), cisplatin, carboplatin or 5-FU treated mice although the values for mice given 5-FU in all cases were considerably lower than for the other chemotherapeutic agents.

The test results presented herein demonstrate that administration of misoprostol and/or other E-type prostaglandins, prior to administration of various chemotherapeutic agents provides protection of various normal tissues from injury or cell death caused by the chemotherapeutic agent. Although all of the E-type prostaglandins may not be effective in protecting all normal tissue from injury or cell death caused by every chemotherapeutic agent, one skilled in the art, in view of the present disclosure and methodology therein, would be able to determine which E-type prostaglandins are effective from protecting which tissues from injury or cell death caused by different chemotherapeutic agents. Furthermore from the results of the testing disclosed herein, it can be postulated that administration of combinations of more than one E-type prostaglandins would be at least as beneficial as administration of one such E-type prostaglandin in protecting normal tissue from injury and/or cell death depending on: 1) the presence of receptors within any given tissue for any E-type prostaglandin; 2) the types of receptors within a given tissue; and 3) the combination of chemotherapeutic agents. Such E-type prostaglandin induced normal tissue protection, as disclosed herein, would be beneficial to patients undergoing chemotherapy treatments, in that it could be expected that such tissue protection would result in reduced side-effects and increase the quality of life, and the longevity of such patients.

What is claimed is:

1. A method for protecting non-stomach and ion-duodenal tissue in a mammal from injury resulting from chemotherapeutic agents comprising, administering prior to the administration of such chemotherapeutic agent, a therapeutically effective amount of an E-type prostaglandin.

2. A method as recited in claim 1 for protecting tissue from injury resulting from chemotherapeutic agents comprising, administering prior to the administration of such chemotherapeutic agent, an E-type prostaglandin selected from the group consisting of:

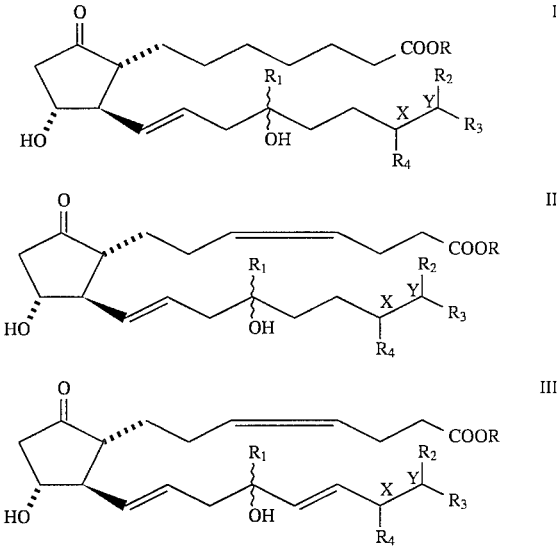

16,16-dimethyl PGE₂; and PGE₁, wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X–Y bond can be saturated or unsaturated.

3. A method as recited in claim 2 wherein the E-type prostaglandin is administered 1 to 3 hours prior to administration of the chemotherapeutic agent.

4. A method as recited in claim 2 wherein the E-type prostaglandin is administered topically.

5. A method as recited in claim 4 wherein the E-type prostaglandin is administered 1 to 3 hours prior to administration of the chemotherapeutic agent.

6. A method as recited in claim 2 wherein the E-type prostaglandin is (±)methyl 7-[3α-hydroxy-2β-(4R-hydroxy-4-methyl-1E, 5E,7E-nonatrienyl)-5-oxo-1α-cyclopentyl]-4Z-heptenoate, or 16,16-dimethyl $PGE_2$.

7. A method as recited in claim 6 wherein the E-type prostaglandin is administered in a dose of from about 0.01 μg/kg to about 50 μg/kg/day.

8. A method as recited in claim 7 wherein the E-type prostaglandin is administered topically.

9. A method as recited in claim 6 wherein the E-type prostaglandin is administered 1 to 3 hours prior to administration of the chemotherapeutic agent.

10. A method as recited in claim 2 wherein the E-type prostaglandin is 16,16-dimethyl $PGE_2$.

11. A method as recited in claim 10 wherein the E-type prostaglandin is administered in a dose of from about 0.01 μg/kg to about 50 μg/kg/day.

12. A method as recited in claim 10 wherein the E-type prostaglandin is administered topically.

13. A method as recited in claim 10 wherein the E-type prostaglandin is administered 1 to 3 hours prior to administration of the chemotherapeutic agent.

14. A method as recited in claim 2 wherein the E-type prostaglandin is misoprostol.

15. A method as recited in claim 14 wherein the E-type prostaglandin is administered in a dose of from about 0.01 μg/kg/day to about 50 μg/kg/day.

16. A method as recited in claim 14 wherein the E-type prostaglandin is administered topically.

17. A method of protecting cells of normal tissue in a mammal from cell death resulting from chemotherapeutic agents comprising, administering, prior to the administration of the chemotherapeutic agent, a therapeutically effective amount of an E-type prostaglandin.

18. The method of claim 17 wherein the E-type prostaglandin is administered from about 1 to about 3 hours prior to administration of the chemotherapeutic agent.

19. A method for protecting tissue in a mammal from injury resulting from chemotherapeutic agents comprising, administering prior to the administration of such chemotherapeutic agent, a therapeutically effective amount of two or more E-type prostaglandins.

20. A method as recited in claim 19 wherein the E-type prostaglandins administered are misoprostol and $PGE_1$.

* * * * *